(12) United States Patent
Kozam et al.

(10) Patent No.: US 6,496,827 B2
(45) Date of Patent: Dec. 17, 2002

(54) METHODS AND APPARATUS FOR THE CENTRALIZED COLLECTION AND VALIDATION OF GEOGRAPHICALLY DISTRIBUTED CLINICAL STUDY DATA WITH VERIFICATION OF INPUT DATA TO THE DISTRIBUTED SYSTEM

(75) Inventors: Marc L. Kozam, Silver Spring, MD (US); Louis Y. Korman, Rockville, MD (US)

(73) Assignee: MLK Software, Sandy Spring, MD (US)

( * ) Notice: Subject to any disclaimer, the term of this patent is extended or adjusted under 35 U.S.C. 154(b) by 0 days.

(21) Appl. No.: 09/423,378

(22) PCT Filed: May 12, 1998

(86) PCT No.: PCT/US98/09590

§ 371 (c)(1),
(2), (4) Date: Jan. 28, 2000

(87) PCT Pub. No.: WO98/52113

PCT Pub. Date: Nov. 19, 1998

(65) Prior Publication Data

US 2002/0035570 A1 Mar. 21, 2002

Related U.S. Application Data

(60) Provisional application No. 60/046,214, filed on May 12, 1997.

(51) Int. Cl.[7] ............................................... G06F 17/30
(52) U.S. Cl. ............................................ 707/10; 705/2
(58) Field of Search .................................. 707/102, 103, 707/104, 4, 10; 709/328; 345/326; 705/2, 3

(56) References Cited

U.S. PATENT DOCUMENTS

| 3,576,433 | A | | 4/1971 | Lee et al. | |
|---|---|---|---|---|---|
| 4,868,866 | A | | 9/1989 | Williams, Jr. | |
| 5,179,660 | A | | 1/1993 | Devany et al. | |
| 5,737,539 | A | * | 4/1998 | Edelson et al. | 705/2 |
| 5,991,731 | A | * | 11/1999 | Colon et al. | 705/2 |
| 5,999,908 | A | * | 12/1999 | Abelow | 434/118 |

FOREIGN PATENT DOCUMENTS

WO        WO 96/08779        3/1996

OTHER PUBLICATIONS

"JetForm Announces First Java(TM)–Based Electronic Forms Solution" JetForm Corporation Press Release, http://www.jetform.com/pressroom/1996/prir961022.html, pp. 1–3.

B. Smith et al, "In Good Electronic Form", 4465 BYTE, Peterborough, NH, US, Nov. 18, 1993, pp. 67–68, 70, 72, 74, and 76; XP000408878.

T.J. Fan et al, "FormPlus: A Form Authoring Toolkit", Proceedings The Fourteenth Annual International Computer Software & Applications Conference, Oct. 31–Nov. 2, 1990, IEEE Computer Society Press, pp. 255–260; XP000223616.

* cited by examiner

*Primary Examiner*—Jack Choules
(74) *Attorney, Agent, or Firm*—Shanks & Herbert

(57) ABSTRACT

The centralized collection of geographically distributed data is accomplished using a system which takes advantage of an interactive programming language, such as Java® and existing wide area networks, such as the Internet including the world wide web (4), to collect high quality data in an information center (10). The information center being connected to remote sites (1) through the wide area network. One or more levels of validation of the data prior to storage in a database is provided for.

30 Claims, 1 Drawing Sheet

METHODS AND APPARATUS FOR THE CENTRALIZED COLLECTION AND VALIDATION OF GEOGRAPHICALLY DISTRIBUTED CLINICAL STUDY DATA WITH VERIFICATION OF INPUT DATA TO THE DISTRIBUTED SYSTEM

This application claims the benefit of Provisional Application Serial No. 60/046,214 filed May 12, 1997.

TECHNICAL FIELD AND INDUSTRIAL APPLICABILITY OF INVENTION

The present invention relates to a method and apparatus for the centralized collection of geographically distributed data. In particular, the invention provides for a method of gathering data that provides interactivity and uses an existing wide area network in the collection of data, while providing high quality data collection with immediate validation of data. Accordingly, the invention is particularly applicable to any enterprise wherein it is useful to collect and maintain data for subsequent study or analysis. It is extremely useful for institutions or businesses wishing to amass data for prospective studies, such as clinical trials for pharmaceuticals.

BACKGROUND OF THE INVENTION

Previously information gathering and data transmission has taken several forms. For example, an individual or member of a group may be given a questionnaire for completion and asked to deliver the completed questionnaire to a central location for tabulation or other processing.

Information (i.e., data), once obtained, may then be transmitted to a central or primary location in several ways. The data, if on paper, may be mailed or perhaps facsimile transmitted to the central location where it is received and further processed. Using a computer system, the information may be encrypted on a computer diskette and mailed to a central location or transmitted by modem. Data on the diskette is then input to a database, for example, where it is electronically stored for further processing. This type of data gathering has a number of drawbacks. One major problem is that the database must be able to accept information deriving from various diskette styles and from diverse computer types or platforms, or the information can only be gathered in this manner by machines which are compatible in their document processing formats. The only other option is to transmit the computer readable data in a plain ASCII format.

As a result, for any study using a large number of data gathers, such as a clinical trial, the data is usually transmitted in paper form to be read and input to a computer database by another individual.

Over the years, the medical profession has widely used information collection and analysis to determine, for example, if procedures being performed are achieving the desired or expected results. Factors relating to both demographic and clinical data are needed to accurately report on completed procedures. Data ranging from the patient information such as age, weight, gender and so on, must be known as well as other information such as the symptoms experienced by the patient, methods used to perform the procedure, tools used, biopsies performed, measurements taken as well as other more detailed clinical information.

In some instances, obtaining information regarding medical procedures can be relatively straight forward. For example, due to the high cost of equipment and staff involved, heart transplants are performed at relatively few medical facilities. Thus, these facilities can be more easily networked to enable access to a central database where results and demographics can be collected and processed. For example, it is physically possible and not too onerous to visit each site where heart transplants are performed and install computer software, and provide training to the hospital staff regarding how to gather and enter the clinical and demographic information into the hospital-based terminals. The information may then be transmitted to a central site via a private wide area network for processing or for inclusion into a database to be available for review and study.

When information must be collected from a great many locations, the above systems are not practical. The cost of installing a private wide area network is typically prohibitive. For instance, many medical procedures are implemented throughout the world, in virtually any hospital or medical operating facility. For example, eye lens replacement (cataract) surgery and gastrointestinal endoscopic procedures are practiced or performed on an "out-patient," same day surgery basis throughout not only the United States, but the world, in facilities such as local or community hospitals or even stand alone out-patient surgical units. Thus, it is impractical and expensive to visit each and every site, install compatible software, and provide training for its use at such a large number of sites. In addition, each upgrade in software would require the same extensive visiting and dissemination. Moreover, the chances of erroneous information being entered into a system are greatly increased as the number of entry sites is expanded.

In addition to the medical community and research centers collecting data for studies, pharmaceutical companies are required to collect data in vast multi-center sites in order to obtain regulatory approval for their drugs. Clinical studies for drug approval require dose ranging and efficacy studies which are usually carried out in sites around the globe such as in the United States, Europe, Canada and Australia. Typically, the pharmaceutical company together with the United States Food and Drug Administration develops the strategy to study the effect of the drug or vaccine. This results in a protocol which is disseminated to all physicians and sites involved in the study. The information is then gathered and recorded by hand in the filling out of a form. These forms, with all of their possible human data entry mistakes and bad handwriting, are then sent to the pharmaceutical company to be rerecorded and entered into a computer as data for statistical analysis.

The gathering of the information at the sites is tedious and is extremely expensive for the pharmaceutical companies. In addition, when there is inaccurate data or unusable data, i.e., invalid data, entire studies can be in jeopardy. Due to the difficulties in obtaining patients for studies, it is imperative to be able to use all the data so as to have a statistically significant result; when data is invalid through errors in recording, studies can be lost.

Accordingly, a need exists for an effective means for gathering geographically distributed data that is valid and will permit the use of the data in either prospective or retrospective studies. In addition, the method or system should make use of existing wide area networks and be compatible with readily available hardware and software so as to provide a cost effective means of gathering the data. Such a means is provided by the method and system of the present invention.

SUMMARY OF THE INVENTION

It is therefore a principle object of the invention to provide a method and apparatus for the centralized collection of geographically distributed data.

It is a further object of the invention to solve the above identified problems in the field.

The present invention solves the problems noted above by providing a data gathering, validation/verification and transmission system that may be easily, and at minimal cost, made available to substantially all practitioners in a field regardless of geographic location Moreover, the system is designed to be utilized by even non-computer-literate individuals in the general population.

The present invention provides an interactive method for the centralized collection of geographically distributed data using an existing wide area network. The method accommodates for data being input from diverse computer types and platforms via the use of a universal interactive programming language, such as JAVA®. In addition, the method assures that the collected data is of the highest quality due to immediate validation during the gathering process, and prior to acceptance and storage in the database.

Accordingly, the present invention provides a method for the centralized collection of geographically distributed data comprising: receiving data from the at least one user with the remote site computer; checking the data for validity with the remote site computer; providing the user an opportunity to correct any invalid data found during the checking; transmitting the data to a centralized computer over a transmission medium; receiving and validating the data from the remote site computer at the centralized computer, including comparing the data to data already stored at the centralized computer to determine if it is valid or invalid; if the data from the remote site computer is determined to be invalid, then performing the following until all data is determined to be valid: signaling with the centralized computer to the remote site computer to provide the user an opportunity to correct invalid data; transmitting corrected data from the remote site computer to the centralized computer; and receiving and validating the corrected data from the remote site computer at the centralized computer, including comparing the corrected data to data already stored at the centralized computer to determine if it is valid or invalid; when all data has been determined to be valid, then entering and storing the valid data in a central database at the centralized computer.

DETAILED DESCRIPTION OF A PREFERRED EMBODIMENT OF THE INVENTION

Figure 1:
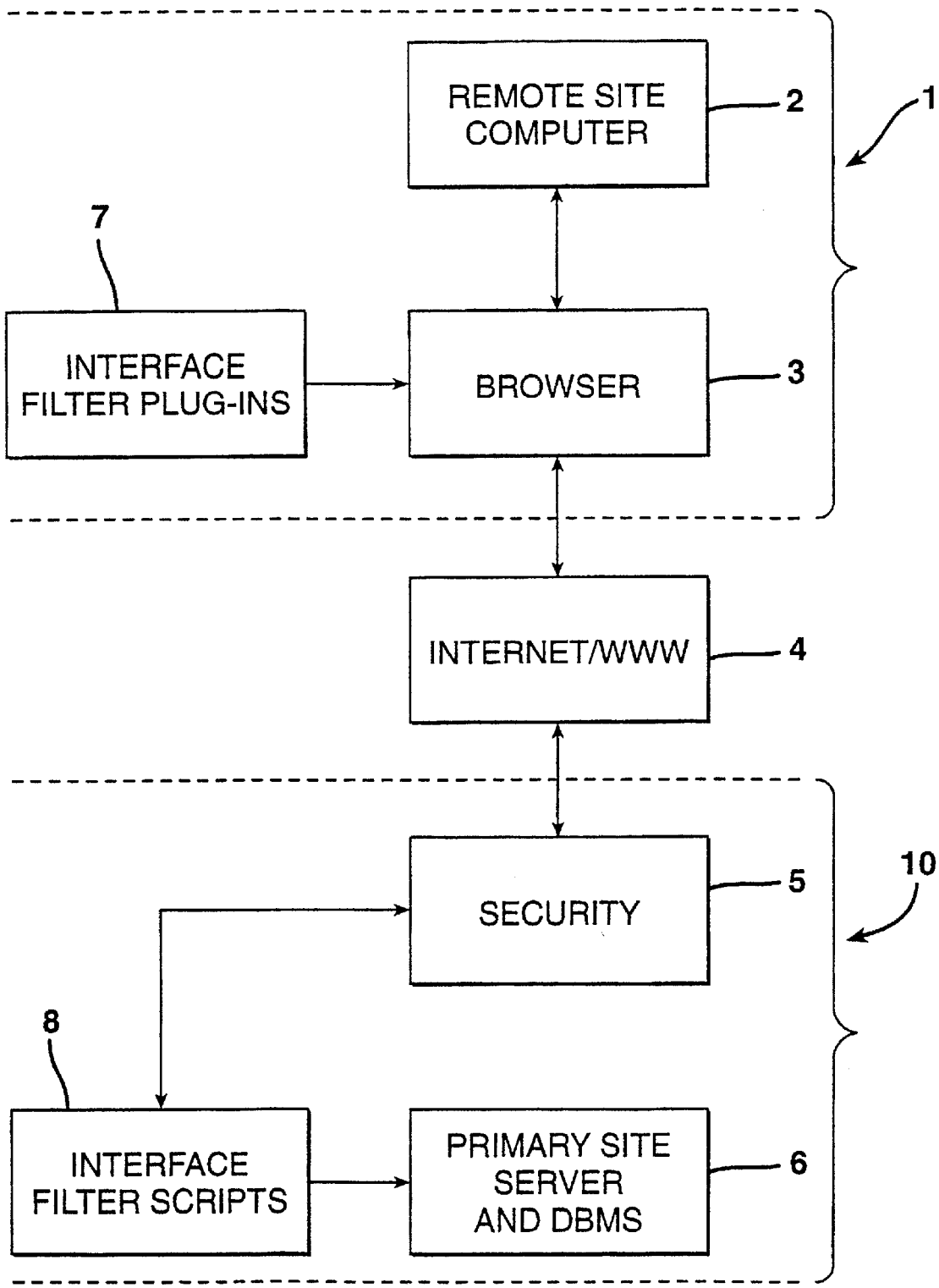
FIG. 1 is a functional block diagram showing an exemplary embodiment of the invention.

The invention will now be described in more detail by way of example with reference to the embodiment shown in the accompanying figure. It should be kept in mind that the following described embodiment is only presented by way of example and should not be construed as limiting the inventive concept to any particular physical configuration.

While the invention will be discussed with specific reference to the medical profession, this is for convenience only. The invention is applicable to any profession and business wanting to collect high quality data. For example, the invention may be used to collect information following such diverse practices as appliance repairs, automotive repairs and lawn mower sales. After the repair of an appliance, needed information may be input at a terminal describing demographics relative to the appliance, the location, and or the owner can be entered and transferred to a central location. Also, data concerning the repair may also be entered and transmitted. Similarly, the type of lawn mower, the size of the lawn owned by the purchaser and optional equipment purchased (bagging or mulching attachment for instance) can be input and correlated with other, earlier entered data. This would give the manufacturer and distributor constantly updated information on sales and customer needs to direct future design, manufacturing and inventory planning.

This invention, however, has a specific use in the medical profession for several reasons. It is important to track an individual patient to be able to ascertain, for example, if a recently completed procedure had been performed previously on that patient. If so, it is desirable to be able to check the personal information to determine if there have been significant changes in the patient. Has it been 10 years or 10 days since the procedure was last performed? Has the patient's weight changed significantly or not at all? This invention verifies data both as it is input by the user as well as when it is received at a central or primary collection point. Also, information regarding surgery performed on similar patient types can be easily reviewed and analyzed for future use. A multitude of other information may also be gathered.

The general plan for implementation of the method of the present invention is as follows. Initially, it is necessary to define the information desired to be collected. For example, in a clinical trial, the protocol or study design will define the information to be collected. Then, the information is broken down into each variable with the parameters defined for validation of that variable. These parameters and validation criteria are then programmed. In particular, the invention uses a programming language that is: optimized for use with browsers; suited for interactive applications; platform independent; relatively concise; and downloadable through a browser. A particularly preferred such language is JAVA®.

An interactive programming language offers several advantages. Packets (applets in Java®) containing the various questionnaires to be completed are loaded at the primary site server or web site and are transmitted to the various remote site locations on a "when needed" basis. Thus, it is not necessary to physically visit each individual remote site to install software. Moreover, it is not necessary to visit each site for usage training because the system is very user friendly. The user's computer is capable of connecting to the internet and the user's browser is capable of processing interactive programming language, thus instructions and advice appear on their monitor as necessary.

Also, because interactive programming uses small packets or applets, changes or updates to the programming are easily accomplished. Moreover, only those packets that are needed to complete a specific questionnaire or form are downloaded by the user. Because the programming is interactive, questions are displayed and answered by the user on a user screen, with the answer being transmitted or delivered to the designated location.

User interfaces or screens are created for collecting and validating each element or field variable of the data. For example, user interface screens are designed using programming languages such as JAVA® and HTML. Once again, the languages used to create the user interface or screens should be: optimized for use with browsers; relatively concise; suited for interactive applications; and downloadable through a browser.

All of the elements or fields are then assembled into a collection or form. Another level of validation is then carried out. The validated data is then transmitted to the central site or database, defined for central storage of the collected, verified data. Databases range from a file to the traditional server. However, the invention contemplates any method of centralized storage that allows for entry and storage of data. In particular, the invention uses the PERL programming language for storage of the data. An additional level of validation is then carried out wherein the previously validated data is checked against the database to determine whether it is to be accepted or returned to the user.

The information or data, as discussed above, is input to and stored in a primary database from which it may be retrieved for processing using a database management system. To be useful, however, the database must be provided with accurate information (data) from all sources where that information can originate; i.e., from virtually all sites where the procedures are being performed. The inventive system includes a means to verify the information at input to reduce, and filter out incorrect information from being transmitted for inclusion into the database. Moreover, the information is further validated against previously stored data. This additional level of validation allows for preventing duplicate data from being entered. It also provides an additional level of validation regarding the accuracy of the data.

The invention further includes security, e.g., a firewall, to exclude unwarranted intrusion and to protect personal information from being improperly accessed.

Referring specifically to the FIGURE, an exemplary embodiment of the overall system according to the invention is shown diagramatically. Only one remote site computer 2, e.g., a personal computer, is shown; however, it is to be understood that any number of personal computers may be used, each one connected, via a wide area network such as the internet, to an information center 10 which includes a research database. The remote site computer(s) 2 would typically be geographically distributed at various different locations which could be anywhere in the world.

Very basically, an exemplary embodiment of the apparatus according to the invention comprises a system having at least one remote site personal computer 2 which can use a browser 3 to connect to a wide area network, e.g., the internet including the world wide web 4. The remote site computer 2 has the browser 3 installed therein, or in a remote site server (not shown). The browser 3 operates as is well known in the art to enable communication and connection of the remote site computer 2 to a wide area network, such as the internet and world wide web 4. The wide area network, such as the internet 4, is also connected, through a security system 5, e.g., a security firewall, and interface filter scripts 8, to a centralized computer system, i.e., a primary site server 6 at the information center 10. The server 6 includes a database management system (DBMS) that collects and stores all information that is accepted in a database. The server database management system (DBMS) allows for access to the information within the database and processing thereof. The primary site server 6 may be embodied as a web site in which a form to be completed with information to be stored in the database is accessed from the web site's home page, for example.

An advantageous aspect of the invention is the provision of one or more validation/verification operations on the data. The embodiment illustrated provides for two separate validation/verification operations represented by interface filter plug-in block 7 and interface filter scripts block 8. A verification/validation is provided by interface plug-in block 7 at the remote site computer 2, and may be implemented as an add-on part of browser 3. The interface filter plug-in 7 at the remote site verifies information as it is entered in remote site computer 2. A second verification/validation is provided by interface filter scripts block 8 to verify information prior to it being committed to and stored in the database at the primary site server 6 at the information center 10. The separate operations of blocks 7 and 8 are explained below.

The above disclosed system provides for a very efficient and effective system to collect information, and to verify collected information for accuracy, both at the input side and collection side of the system.

As illustrated, at remote site computer 2 is an interface filter plug-in 7. The interface filter plug-in 7 provides for a first validation check of the data being entered at remote site computer 2. The interface filter plug-in 7 preferably checks information as it is entered; i.e., as questions are answered or fields of a form are filled in, as they appear on the monitor (not shown) of the remote site computer 2. For example, if the question/field is regarding a person's age, the interface plug-in filter 7 would instantly ask a user for confirmation of the input data if, for example, the input for that answer/field, because of a typo, was "150" years old. Clearly this data is easily recognizable by the interface plug-in filter 7 as an error which should be immediately corrected by the user.

Also, the interface plug-in filter 7 may be configured to check one answer/field, or a series of answers/fields, against other answers/fields. For example, if a person's weight is entered as 10 pounds but the person is also listed as being 35 years old, the interface plug-in filter 7 could query the user entering the information at the remote site computer 2 to correct the input data in one or both answers/fields.

An interface filter scripts block 8 is provided as a plug-in at the information center 10, and block 8 operates to filter and validate, and in particular, to check the data received from the remote site computer 2 against data already in storage in the database at the information center 10. For example, before entering new information into the database, a check is made to determine if the same information has previously been delivered to and stored in the database. Further, as another example, if the system is being used to track medical procedures, it would be important to determine if the patient were treated previously using the same procedure, or a different but related procedure at another remote site. Interface filter block 8 would operate to instruct the primary site server 6 to check if the patient in question, using a unique identifier, e. g, driver's license number, has previously reported information stored within the database.

It will be apparent to one skilled in the art that the manner of making and using the claimed invention has been adequately disclosed in the above-written description of the preferred embodiments taken together with the drawing.

It will be understood that the above described preferred embodiment of the present invention is susceptible to various modifications, changes, and adaptations, and the same are intended to be comprehended within the meaning and range of equivalents of the appended claims.

What is claimed is:

1. A computer-based method for centralized collection of geographically distributed information from at least one user at a remote site computer, comprising:

obtaining data from a clinical trial;

receiving said clinical trial data from the at least one user with the remote site computer;

checking the data for validity with the remote site computer;

providing the user an opportunity to correct any invalid data found during the checking;

transmitting the data to a centralized computer over a transmission medium;

receiving and validating the data from the remote site computer at the centralized computer, including comparing the data to data already stored at the centralized computer to determine if it is valid or invalid;

if the data from the remote site computer is determined to be invalid, then performing the following until all data is determined to be valid:

signaling with the centralized computer to the remote site computer to provide the user an opportunity to correct invalid data;

transmitting corrected data from the remote site computer to the centralized computer; and receiving and validating the corrected data from the remote site computer at the centralized computer, including comparing the corrected data to data already stored at the centralized computer to determine if the data is valid or invalid;

when all data has been determined to be valid, then entering and storing the valid data in a central database at the centralized computer.

2. The method according to claim 1, wherein the receiving data from the at least one user with the remote site computer comprises displaying a form having fields to the user into which the data is entered field by field;

wherein the checking the data for validity with the remote site computer comprises checking the data as it is entered in a field by the user; and wherein the providing the user an opportunity to correct any invalid data found during the checking comprises signaling the user that data entered in a field may be invalid.

3. The method according to claim 2, wherein the checking the data for validity with the remote site computer comprises checking the data after data has been entered by the user into all fields of the form.

4. The method according to claim 1, wherein the transmitting the data to a centralized computer over a transmission medium comprises:

sending the data from the remote site computer to the centralized computer via the internet.

5. The method according to claim 1, wherein the method further comprises:

establishing a connection between the remote site computer and the centralized computer via the internet using a browser having interface filter plug-ins.

6. The method according to claim 5, wherein the interface filter plug-ins provide the checking the data for validity with the remote site computer.

7. The method according to claim 5, wherein the receiving and validating the data from the remote site computer to determine if the data is valid or invalid is performed using interface filter scripts.

8. The method according to claim 5, wherein the remote site computer and the centralized computer are programmed to perform the method using a programming language optimized for use with the browser, suitable for interactive applications, platform independent, relatively concise and downloadable through a browser.

9. The method according to claim 8, wherein the programming language comprises JAVA®.

10. The method according to claim 1, wherein the user can customize the database fields and format.

11. A computer-based system to gather, transmit, and store geographically distributed information comprising:

input means for entry of information at a remote site;

an information center having receiving means for receiving and storing the information;

transmission means for transmitting the entered information to the receiving means from the remote site input means;

first verification means at the remote site for verifying the information for accuracy as the information is being entered with the input means;

second verification means at the information center for verifying the information received from the remote site input means by comparing the information with information previously stored at the information center;

wherein at least one of the first verification means and the second verification means comprises means for verifying the information for accuracy as clinical trial data against a predetermined clinical trial data variable.

12. The apparatus in accordance with claim 11, wherein both of the first verification means and the second verification means comprise means for verifying the information for accuracy as clinical trial data against a predetermined clinical trial data variable.

13. The apparatus of claim 12, wherein said input means at said remote site comprises a computer having data entry means for entering data, a central processing means for processing data, and a display means for displaying data.

14. The apparatus of claim 13, wherein the transmission means comprises a browser running in the computer.

15. The apparatus of claim 14, wherein the receiving means for receiving and storing the information comprises a server including a database and a database management system.

16. The apparatus of claim 15, wherein the transmission means further comprises a wide area network connecting the server and the computer.

17. The apparatus of claim 16, wherein the wide area network comprises the internet including the world wide web.

18. The apparatus of claim 12, wherein the first verification means comprises an interface plug-in including a filter.

19. The apparatus of claim 12, wherein second verification means at the information center comprises an interface filter including a script to verify new information against stored information.

20. The apparatus of claim 19, wherein said script comprises Java Script®.

21. The apparatus of claim 12, further including security means for insuring the integrity of the information that is transmitted and that is stored.

22. The apparatus of claim 12, wherein the computer-based system is controlled by an interactive programming language software installed at the information center and accessible by the remote site.

23. The apparatus of claim 22, wherein said interactive programming language comprises the Java® programming language.

24. The apparatus of claim 12, wherein the user has access to worldwide real-time clinical trial data.

25. A computer system for clinical trial management of centralized collection of geographically distributed information, comprising:

a remote site computer having a browser with a first data verification module for verifying data entered at the remote, site computer;

a transmission medium coupled to the remote site computer; and a central computer coupled to the transmission medium, and having a database and a second data verification module for verifying data received from the remote site computer;

wherein at least one of the first verification module and the second verification module comprises means for verifying the information for accuracy as clinical trial data against a predetermined clinical trial data variable.

26. The computer system according to claim 25, further comprising a plurality of remote site computers, each having a browser with a first data verification module for verifying data entered at the respective remote site computer, and each remote site computer being coupled to the transmission medium.

27. The computer system in accordance with claim 25, wherein both of the first verification module and the second verification module comprise means for verifying the information for accuracy as clinical trial data against a predetermined clinical trial data variable.

28. An interactive computer web-enabled method for use in clinical trial research using centralized collection of geographically distributed information from at least one user at a remote site computer, comprising:

obtaining data from a clinical trial;

receiving said data from the at least one user with the remote site computer;

checking the data for validity with the remote site computer;

providing the user an opportunity to correct any invalid data found during the checking;

transmitting the data to a centralized computer over a transmission medium;

receiving and validating the data from the remote site computer at the centralized computer, including comparing the data to data already stored at the centralized computer to determine if it is valid or invalid;

if the data from the remote site computer is determined to be invalid, then performing the following until all data is determined to be valid:

signaling with the centralized computer to the remote site computer to provide the user an opportunity to correct invalid data;

transmitting corrected data from the remote site computer to the centralized computer; and receiving and validating the corrected data from the remote site computer at the centralized computer, including comparing the corrected data to data already stored at the centralized computer to determine if the data is valid or invalid;

when all data has been determined to be valid, then entering, storing, and providing physicians real time access to the valid data in a central database at the centralized computer to allow them to react quickly to the patient's symptoms.

29. A web-enabled clinical trial management system for gathering, transmitting, and storing geographically distributed information comprising:

input means for entry of information at a remote site;

an information center having receiving means for receiving and storing information;

transmission means for transmitting the entered information to the receiving means from the remote site input means;

first verification means at the remote site for verifying the information for accuracy as the information is being entered with the input means; and second verification means at the information center for verifying the information received from the remote site input means by comparing the information with information previously stored at the information center;

wherein at least one of the first verification means and the second verification means comprises means for verifying the information for accuracy as clinical trial data against a predetermined clinical trial data variable.

30. The system in accordance with claim 29, wherein both of the first verification means and the second verification means comprise means for verifying the information for accuracy as clinical trial data against a predetermined clinical trial data variable.

* * * * *